(12) United States Patent
Narkiss

(10) Patent No.: US 12,324,658 B2
(45) Date of Patent: Jun. 10, 2025

(54) TUBING SYSTEM WITH OPERATION MODE COMMUNICATION

(71) Applicant: Oridion Medical 1987 Ltd., Jerusalem (IL)

(72) Inventor: Nadav Narkiss, Be'er Ya'akov (IL)

(73) Assignee: Oridion Medical 1987 Ltd. (IL)

( * ) Notice: Subject to any disclaimer, the term of this patent is extended or adjusted under 35 U.S.C. 154(b) by 0 days.

(21) Appl. No.: 18/351,854

(22) Filed: Jul. 13, 2023

(65) Prior Publication Data

US 2023/0355132 A1    Nov. 9, 2023

Related U.S. Application Data

(62) Division of application No. 16/390,869, filed on Apr. 22, 2019, now Pat. No. 11,701,029.

(Continued)

(51) Int. Cl.
*A61B 5/083*    (2006.01)
*A61B 5/097*    (2006.01)
(Continued)

(52) U.S. Cl.
CPC ............ *A61B 5/0836* (2013.01); *A61B 5/097* (2013.01); *A61M 16/024* (2017.08);
(Continued)

(58) Field of Classification Search
CPC . A61B 5/0836; A61B 5/097; A61B 2560/028; A61B 2562/226;
(Continued)

(56) References Cited

U.S. PATENT DOCUMENTS 6,656,127 B1 *  12/2003  Ben-Oren ............. H01J 65/042
                                                           600/529
6,935,338 B1 *   8/2005  Triunfo, Jr. ......... A61M 16/085
                                                         128/204.22

(Continued)

OTHER PUBLICATIONS

International Application No. PCT/IL2019/050460 International Search Report and Written Opinion dated Sep. 30, 2019, 20 pages.

(Continued)

*Primary Examiner* — Joseph D. Boecker
(74) *Attorney, Agent, or Firm* — Draft Masters IP, LLC

(57) ABSTRACT

A capnography system includes a $CO_2$ sensing system having a $CO_2$ sensor configured to measure a $CO_2$ concentration in exhaled breath of a subject, a processor configured to derive one or more breath related parameters based on the measured $CO_2$ concentration, and a communication unit. The capnography system includes a tubing system configured to allow flow of respiratory gasses therethrough. The tubing system includes a connector configured to connect the tubing system to the $CO_2$ sensing system and a communication component configured to provide an indication of a type of the tubing system to the communication unit. The communication unit is configured to transfer data to the processor based on the indication obtained from the communication component, and the processor is configured to change or suggest a change of an operation mode of the $CO_2$ sensing system based on the data.

14 Claims, 3 Drawing Sheets

Related U.S. Application Data

(60) Provisional application No. 62/661,732, filed on Apr. 24, 2018.

(51) Int. Cl.

| | | |
|---|---|---|
| *A61M 13/00* | (2006.01) | |
| *A61M 16/00* | (2006.01) | |
| *A61M 16/04* | (2006.01) | |
| *A61M 16/06* | (2006.01) | |
| *A61M 16/08* | (2006.01) | |
| *A61M 39/10* | (2006.01) | |

(52) U.S. Cl.
CPC ...... *A61M 16/0411* (2014.02); *A61M 16/085* (2014.02); *A61M 16/0875* (2013.01); *A61B 2560/028* (2013.01); *A61B 2562/226* (2013.01); *A61M 13/003* (2013.01); *A61M 2016/0413* (2013.01); *A61M 16/0493* (2014.02); *A61M 16/0672* (2014.02); *A61M 2039/1022* (2013.01); *A61M 2202/0208* (2013.01); *A61M 2202/0225* (2013.01); *A61M 2205/18* (2013.01); *A61M 2205/273* (2013.01); *A61M 2205/276* (2013.01); *A61M 2205/3592* (2013.01); *A61M 2205/502* (2013.01); *A61M 2205/6018* (2013.01); *A61M 2230/432* (2013.01)

(58) Field of Classification Search
CPC .... A61B 2562/227; A61M 2016/0413; A61M 2202/0225; A61M 16/024; A61M 16/04; A61M 16/0411; A61M 16/0493; A61M 16/0666; A61M 16/0672; A61M 16/085; A61M 2205/273; A61M 2230/432; A61M 13/003
See application file for complete search history.

(56) References Cited

U.S. PATENT DOCUMENTS

| | | | |
|---|---|---|---|
| 2006/0278221 A1* | 12/2006 | Schermeier | A61M 16/0875 128/204.23 |
| 2008/0027344 A1 | 1/2008 | Terry | |
| 2008/0200776 A1 | 8/2008 | Schermeier et al. | |
| 2008/0251070 A1 | 10/2008 | Pinskiy et al. | |
| 2009/0275851 A1* | 11/2009 | Colman | A61M 16/0497 128/205.24 |
| 2010/0317986 A1* | 12/2010 | Colman | A61B 5/082 600/532 |
| 2011/0040713 A1* | 2/2011 | Colman | A61B 5/0836 703/2 |
| 2011/0265793 A1 | 3/2011 | Haveri | |
| 2014/0014729 A1* | 1/2014 | Colman | G06K 19/07758 235/487 |
| 2014/0187985 A1 | 7/2014 | Corl et al. | |
| 2015/0192234 A1* | 7/2015 | Fries | A61M 39/10 285/9.1 |
| 2015/0265828 A1* | 9/2015 | Colman | F16L 21/00 604/535 |
| 2015/0289085 A1 | 10/2015 | Shelly et al. | |
| 2015/0306365 A1* | 10/2015 | Besko | A61M 39/10 604/111 |
| 2016/0003733 A1* | 1/2016 | Goldberg | G01N 21/21 359/486.03 |
| 2016/0073929 A1* | 3/2016 | Weiss | A61B 5/097 600/543 |
| 2016/0093205 A1* | 3/2016 | Boyer | A61B 5/02416 340/506 |
| 2016/0231309 A1 | 11/2016 | Ahmad et al. | |
| 2017/0224975 A1* | 8/2017 | Peer | A61M 39/10 |
| 2017/0273597 A1 | 9/2017 | Schuelke et al. | |
| 2017/0325716 A1* | 11/2017 | Coleman | A61B 5/082 |
| 2019/0320938 A1 | 10/2019 | Narkiss | |

OTHER PUBLICATIONS

Prosecution History from U.S. Appl. No. 16/390,869, dated May 25, 2022 through Mar. 9, 2023, 84 pp.

"Requisition", Canadian Application No. 3096456, Apr. 9, 2025, 5pgs.

* cited by examiner

TUBING SYSTEM WITH OPERATION MODE COMMUNICATION

CROSS-REFERENCE TO RELATED APPLICATION

This application is a divisional of U.S. application Ser. No. 16/390,869, filed on Apr. 22, 2019, which claims priority to and the benefit of U.S. Provisional Application No. 62/661,732, filed on Apr. 24, 2018, the content of each of which is incorporated herein by reference in its entirety for all purposes.

TECHNICAL FIELD

The present disclosure generally relates to the field of capnography systems and uses thereof.

BACKGROUND

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Measuring respiratory carbon dioxide ($CO_2$) of a subject provides significant indication of metabolic-related conditions of the subject. Common capnography systems that measure respiratory $CO_2$ use the absorption properties of $CO_2$ molecules for electromagnetic waves at certain wavelengths to measure the concentration of $CO_2$ molecules within the respired gas. However, measuring respiratory $CO_2$ may be complicated and/or altered by the tubing system and/or by medical procedures performed during the measuring process.

SUMMARY

The following embodiments and aspects thereof are described and illustrated in conjunction with systems, tools and methods, which are meant to be exemplary and illustrative, not limiting in scope. In various embodiments, one or more of the above-described problems have been reduced or eliminated, while other embodiments are directed to other advantages or improvements.

According to some embodiments, there is provided a capnography system, including a $CO_2$ sensing module and a tubing system. According to some embodiments, the $CO_2$ sensing module may include a $CO_2$ sensor configured to measure the $CO_2$ concentration in a subject's exhaled breath, a processing unit configured to derive one or more breath related parameters based on the measured $CO_2$ concentration, a pump, and a communication unit. According to some embodiments, the tubing system may be configured to allow flow of respiratory gasses therethrough and may include a connector configured to connect the tubing system to the $CO_2$ sensing module and a communication component configured to provide an indication of a type of the tubing system to the communication unit when the tubing system is connected to the $CO_2$ sensing module. Advantageously, the communication unit may be configured to transfer data to the processing unit based on the indication obtained from the communication component, and the processing unit may be configured to change or suggest a change of an operation mode of the $CO_2$ sensing module based on the transferred data.

According to some embodiments, the tubing system may include an intubation tube. According to some embodiments, changing an operation mode of the $CO_2$ sensing module may include enhancing or suggesting an enhancement of the operation of the pump upon intubation and until a first $CO_2$ signal is obtained, thereby reducing a time required for verification of correct intubation.

According to some embodiments, the tubing system may include or be a bite block, and changing an operation mode of the $CO_2$ sensing module may include identifying $CO_2$ concentration peaks resulting from $CO_2$ insufflation of the subject and/or applying/initiating or suggesting use of an algorithm configured to reduce nuisance alarms during insufflation.

According to some embodiments, the tubing system may include or be an oral nasal cannula and changing an operation mode of the $CO_2$ sensing module may include identifying high respiration rates resulting from pain and/or applying/initiating or suggesting use of an algorithm configured to reduce nuisance alarms during pain management.

According to some embodiments, the tubing system may include or be an oxygen supply tube and changing an operation mode of the $CO_2$ sensing module may include identifying aberrations in the $CO_2$ measurements resulting from dilution of the exhaled breath with oxygen and/or applying/initiating or suggesting use of an algorithm configured to correct/normalize/adjust the one or more breath related parameters, based on the identified dilution.

According to some embodiments, the data may be encrypted.

According to some embodiments, the communication component may be further configured to provide a second indication regarding a property of the tubing system to the communication unit, and the processing unit may be further configured to adjust or suggest adjustment of the operation mode of the $CO_2$ sensing module based on the second indication. According to some embodiments, the property of the tubing system may be a length of the tubing system, a diameter of the tubing system, a target group of the tubing system, an intended duration of the tubing system, or any combination thereof.

According to some embodiments, the communication component is further configured to provide a third indication regarding a manufacturing detail of the tubing system to the communication unit. According to some embodiments, the manufacturing detail may include or be production site, production date, production station, lot number, serial number, expiration date, or any combination thereof.

According to some embodiments, the communication component may be further configured to transfer usage data to the communication unit and/or the processing unit. According to some embodiments, the usage data may include or be a number of occlusion of the tubing system, duration of use, number of uses/connections of the tubing system to a $CO_2$ sensing module, or any combination thereof.

According to some embodiments, the processing unit and/or the communication unit may be configured to communicate a signal terminating the usability of the tubing system, when the operational data indicates that the tubing system has run obsolete. According to some embodiments, terminating the usability may include destroying the communication component of the tubing system.

According to some embodiments, the processing unit may be further configured to transfer the operational data and the manufacturing detail to a remote computational unit. According to some embodiments, the remote computational unit may be configured to integrate the operational data with the manufacturing detail, thereby enabling identification of manufacturing problems causing defects in the tubing system and/or enabling identification of defected tubing system prior to their use and/or distribution.

According to some embodiments, the capnography system may further include a user interface (UI) configured to receive the suggested change in the operational mode of the $CO_2$ sensing module and, optionally, to allow a user to implement, adjust, or overrule the suggested change.

According to some embodiments, the communication component comprises a 1-wire electrically erasable programmable read-only memory (EEPROM).

According to some embodiments, there is provided a processing module including computer executable software configured to receive, from a sensing module, an indication of a type of the tubing system connected to the sensing module and to change or to suggest a change of an operation mode of the $CO_2$ sensing module based on the indication.

As a non-limiting example, the processing module may receive an indication that a tubing system including an intubation tube is connected to the $CO_2$ sensing module and accordingly enhance or suggest an enhancement of the operation of a pump functionally connected to the intubation tube, upon intubation and until a first $CO_2$ signal is obtained, thereby advantageously reducing a time required for verification of correct intubation.

As another non-limiting example, the processing module may receive an indication that a tubing system including a bite block is connected to the $CO_2$ sensing module and accordingly apply or suggest applying an algorithm identifying $CO_2$ concentration peaks resulting from $CO_2$ insufflation of the subject, thus advantageously enabling a reduction in nuisance alarms during $CO_2$ insufflation.

According to some embodiments, the data received by the processing module may be encrypted.

According to some embodiments, the processing module may be further configured receive an indication regarding a property of the tubing system to the communication unit, and to trigger or suggest adjustment of an operation mode of the $CO_2$ sensing module, based on the indication. According to some embodiments, the property of the tubing system may be a length of the tubing system, a diameter of the tubing system, a target group of the tubing system, an intended duration of the tubing system, or any combination thereof.

According to some embodiments, the processing module may be further configured receive an indication regarding a manufacturing detail of the tubing system. According to some embodiments, the manufacturing detail may include or be production site, production date, production station, lot number, serial number, expiration date, or any combination thereof.

According to some embodiments, the processing module may be further configured receive usage data of the tubing system including, for example, a number of occlusion of the tubing system, duration of use, number of uses/connections of the tubing system to a $CO_2$ sensing module, or any combination thereof. According to some embodiments, the processing module may be further configured to trigger or suggest adjustment of the $CO_2$ sensing module, based on the usage data.

According to some embodiments, the processing unit may be configured to communicate a signal terminating the usability of the tubing system when the operational data indicates that the tubing system has run obsolete. According to some embodiments, terminating the usability may include destroying the communication component of the tubing system.

According to some embodiments, the processing unit may be further configured to transfer the operational data and the manufacturing detail to a remote computational unit. According to some embodiments, the remote computational unit may be configured to integrate the operational data with the manufacturing detail, thereby enabling identification of manufacturing problems causing defects in the tubing system and/or enabling identification of defected tubing system prior to their use and/or distribution.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions.

BRIEF DESCRIPTION OF THE DRAWINGS

Examples illustrative of embodiments are described below with reference to figures attached hereto. In the figures, identical structures, elements, or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION

Figure 1:
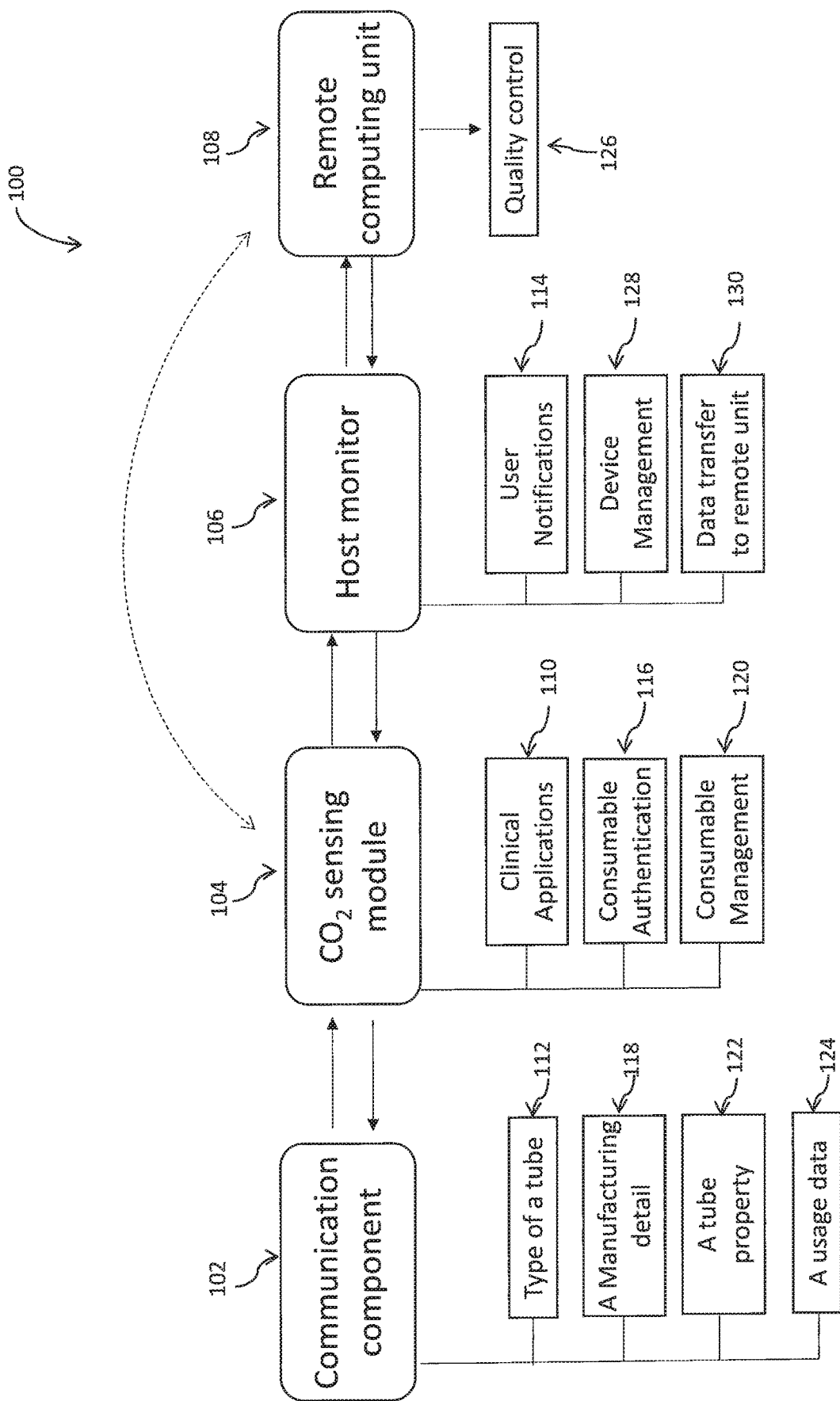
FIG. 1 schematically illustrates a functional block-diagram of a capnography system, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

According to some embodiments, there is provided a capnography system, comprising a $CO_2$ sensing module and a tubing system. The $CO_2$ sensing module includes a $CO_2$ sensor configured to measure a $CO_2$ concentration in a subject's exhaled breath, a processing unit configured to derive one or more breath related parameters based on the measured $CO_2$ concentration, a pump, and a communication unit. The tubing system is configured to allow flow of respiratory gasses therethrough, and includes a connector configured to connect the tubing system to the $CO_2$ sensing module and a communication component configured to provide an indication to the communication unit regarding the type of the tubing system connected. The communication unit is configured to transfer data to the processing unit based on the indication obtained from the communication component. The transferred data is utilized by the processing unit to change or suggest a change of an operation mode of the $CO_2$ sensing module based on the transferred data.

Advantageously, the herein disclosed capnography system enables communication, optionally in both directions, between the tubing system and the $CO_2$ sensing module to which it is connected. This may enable one to specify and/or custom fit the operation mode of the $CO_2$ sensing module according to the tubing system attached and/or its medical application by implementing sample line specific algorithms and/or features based on the type of consumable connected.

According to some embodiments, the communication component may be configured to store, receive, and/or transfer data. Each possibility is a separate embodiment.

According to some embodiments, the communication component may be further configured to provide a second indication regarding a property of the tubing system, such as, but not limited to, a length of a sampling tube, a diameter of the tubing system, a target group of the tubing system, an intended duration of use of the tubing system, or any combination thereof. Each possibility is a separate embodiment. According to some embodiments, the processing unit may be further configured to adjust or suggest adjustment of the operation mode of the $CO_2$ sensing module based on the second indication.

As a non-limiting example, in upper gastro-intestinal procedures requiring use of a bite block, a common problem is the prevalence of spikes in the $CO_2$ concentration measurements due to the insufflation of the patient with $CO_2$. Communication between the bite block tubing and the $CO_2$ sensing module may advantageously enable customizing the operation mode of the $CO_2$ sensing module to implement algorithms, which enable disregarding and/or designating the spikes as artifacts caused by the insufflation, thereby preventing or reducing triggering of nuisance alarms.

Similarly, in emergency settings (EMS), where patients undergo intubation, the appearance of a $CO_2$ reading typically serves as verification of correct intubation. However, when utilizing side stream capnography, the relatively long response time due to the travel of the breath sample through the sampling tube, may delay the verification which may be critical in situations where reintubation is required. Communication between the intubation tubing and the $CO_2$ sensing module may advantageously enable customizing the operation mode of the $CO_2$ sensing module to trigger the increasing of the pumping speed until a first reading is obtained, thereby significantly decreasing the response time and thus the time required for verification of correct intubation. It is noted that an increasing of the pumping speed may be applicable for intubation of adults only. Accordingly, the communication component (whether the same or a different component) may further provide data regarding a property of the attached tube, such as the intubation tube being for use in adults or neonates, and to trigger the increasing of the pumping speed only when an intubation tube for use in adults is connected.

As an additional example, at the general care floor (GCF) and/or post-operative settings, patients suffering from pain and/or undergoing pain management may experience elevated respiration rates that are not associated with pathologic breathing, yet may be interpreted as such and often result in an unnecessary triggering of an alarm. Communication between the breath sampling tubing and the $CO_2$ sensing module may advantageously enable customizing the operation mode of the $CO_2$ sensing module to implement algorithms which enable disregarding and/or designating the elevated respiration rate as an artifact, thereby preventing/reducing the triggering of nuisance alarms.

According to some embodiments, the adjustment and/or change in the operation mode of the $CO_2$ sensing module may be automatically activated by the connection of the specific tubing to the $CO_2$ sensing module without requiring any user intervention or changes on the host monitor design. Alternatively, the sample line specific algorithms and/or features may be in the form of recommendations (for example, presented to the user on a monitor of a UI), and the implementing of the algorithms and/or features may require the consent of the user. By allowing a user feedback, a user may discard/overrule the suggested change or modify it based on the user's professional perception/judgement of the patient's needs.

According to some embodiments, the data may be encrypted. As a non-limiting example, the data transferred by the communication unit to the processing unit and/or to the remote compute unit and vice versa may be encrypted, thereby securing it from user interference.

According to some embodiments, the communication component may be further configured to provide a third indication regarding a manufacturing detail of the tubing system to the communication unit. Non-limiting examples of suitable manufacturing details include production site, production date, production station, lot number, serial number, expiration date, or any combination thereof. Each possibility is a separate embodiment.

According to some embodiments, the communication unit may be further configured to transfer the third indication regarding the manufacturing detail to a remote computing unit for storage and/or further analysis. It is understood that the remote computing unit may use the transferred data for quality control analysis. As a non-limiting example, the remote computing unit may be programmed via software to analyze the manufacturing quality of a particular manufacturing site, by correlating the performance of tubing systems with the manufacturing site. As another non-limiting example, the remote computing unit may be programmed via software to identify tubing systems belonging to a lot with manufacturing defects, by correlating the performance of tubing systems with the manufacturing site. As another non-limiting example, the remote computing unit may be programmed via software to manage production and/or storage parameters by monitoring the serial number, lot number, and/or expiration date of tubing system being used. According to some embodiments, the remote unit may back-communicate user instructions to a user-interphase based on the quality control analysis. For example, once a lot with defects has being identified, plugging in the tubing system belonging to the defect lot may result in a message popping up on the host monitor notifying the user of the defect, optionally in conjunction with a recommendation to discard the tubing system. Additionally or alternatively, the remote unit and/or the user interface may back-communicate data to the communication component of the tubing system itself. As a non-limiting example, plugging in an outdated tubing system may result in an automatic disposal/terminating its usability of the tubing system, thus preventing its misuse. As another non-limiting example, plugging in an outdated tubing system may result in an inactivation of the $CO_2$ sensing module. According to some embodiments, plugging in an outdated tubing system may result in the communication component of the tubing system sending a notification to the $CO_2$ sensing module and/or to the host monitor.

According to some embodiments, the communication component may be further configured to transfer usage data (also referred to herein as performance data) to the $CO_2$ sensing module's communication unit and/or processing unit. Non-limiting examples of suitable usage data include number of occlusions of the tubing system, duration of use, number of uses/connections of the tubing system to a $CO_2$ sensing module, or any combination thereof. Each possibility is a separate embodiment. According to some embodiments, the communication unit may be further configured to transfer the usage data to a remote computing unit (and/or a user interface) for storage and/or further analysis. According to some embodiments, the remote computing unit may use the performance data for quality control analysis. As a non-limiting example, the remote computing unit may be programmed via software to analyze the manufacturing quality of a particular manufacturing site by correlating the performance of tubing systems with the manufacturing site.

According to some embodiments, the communication unit may control the usage of the tubing data based on the transferred performance data during use. As a non-limiting example, the tubing system or the $CO_2$ sensing module may include a pressure sensor configured to detect pressure changes in the tubing system, which pressure changes result from occlusions/blockages in the tubing system. According to some embodiments, once recurring occlusions/blockages of the tubing are identified, the communication unit of the $CO_2$ sensing module may be configured to transfer/trigger a message to pop on up on the host monitor notifying the user of the tubing system having reached saturation, optionally in conjunction with a recommendation to discard the tubing system. Additionally or alternatively, the communication unit may back-communicate data to the communication component causing its abolishment and/or changing its status, thus preventing misuse. As another non-limiting example, the communication component may be configured to transfer the duration of use to the communication unit. The communication unit may then, once an upper limit of use has been reached and/or approaching, trigger a message to pop on up on the host monitor notifying the user of the tubing system having reached saturation, optionally in conjunction with a recommendation to discard the tubing system. Additionally or alternatively, the communication unit may back-communicate data to the communication component causing its abolishment/terminating its usability and/or change its status once an upper limit of use has been reached, thus preventing potentially hazardous continued use of the tubing system.

According to some embodiments, discarding, disposing, abolishing, and terminating the usability of a tubing system may include destroying the communication component of the tubing system, thus preventing it from being recognized by the $CO_2$ sensing module. According to some embodiments, discarding, disposing, abolishing, and terminating the usability of a tubing system may include changing a status (e.g. tube blocked), which change in status may be identified by the $CO_2$ sensing module. According to some embodiments, the change in status may cause/trigger the $CO_2$ sensing module to notify the host monitor of the changed status. According to some embodiments, the change in status may cause inactivation of the $CO_2$ sensing module.

According to some embodiments, the change in status may cause/trigger the $CO_2$ sensing module to notify the host monitor of the changed status.

According to some embodiments, the communication link may include or be a communication bus, such as a serial communication bus. According to some embodiments, the serial communication bus may be a 1-wire bus. According to some embodiments, the serial communication bus may be an EEPROM, such as, but not limited to, a 1-wire EEPROM. According to some embodiments, the serial communication bus may be an inter-integrated circuit ($I_2C$) bus, a universal asynchronous receiver-transmitter (UART) bus, an serial peripheral interface (SPI) bus, or the like. According to some embodiments, the communication link may include near-field communication (NFC) or radio-frequency identification (RFID).

According to some embodiments, the communication unit facilitates a bus communication protocol. According to some embodiments, the communication unit facilitates a master/slave communication protocol, wherein the communication component in the consumable is a communication slave component and the communication unit of the $CO_2$ sensing module is a master communication controller. According to some embodiments, the communication unit is configured to manage the communication on the communication component.

Reference is now made to FIG. 1, which schematically illustrates a functional block-diagram of a capnography system 100, according to some embodiments. According to some embodiments, the capnography system 100 includes a communication component 102 in communication with a $CO_2$ sensing module 104 (e.g., $CO_2$ sensing system). The $CO_2$ sensing module 104 is configured to be in communication with a host monitor 106 and a remote computing unit 108. According to some embodiments, communication of the $CO_2$ sensing module 104 and the remote computing unit 108 utilizes cloud-based security solutions.

The $CO_2$ sensing module 104 is configured to obtain information provided by the communication component 102 regarding a tubing system connected thereto, and analyze it for a clinical application purpose 110, consumable authentication purpose 116, consumable management purpose 120, and/or the like.

According to some embodiments, the $CO_2$ sensing module 104 is configured to identify a desired clinical application 110 based on an indication of a type of a tubing system 112 connected thereto, as received from communication component 102, and to adjust or maintain an operation mode thereof to comply with the desired clinical application. According to some embodiments, the $CO_2$ sensing module 104 changes or suggests a change of the operation mode. According to some embodiments, the $CO_2$ sensing module 104 is further configured to transfer data based on the received indication to the host monitor 106 and/or the remote computing unit 108. According to some embodiments, the $CO_2$ sensing module 104 is configured to trigger a user notification message 114 on the host monitor 106 notifying a user on a suggested operation mode or on a current operation mode or on a change/adjustment of the operation mode, based on the identified desired clinical application. According to some embodiments, a user is allowed to implement, adjust, or overrule the suggested change/adjustment. Optionally, the host monitor 106 allows a user to access a device management unit 128 to control/manage the operation mode. Optionally, the host monitor 106 is configured for data transfer 130 to the remote computing unit 108.

According to some embodiments, the $CO_2$ sensing module 104 is configured for consumable authentication 116 based on a manufacturing detail of a tubing system 118 connected thereto, which is received from the communication component 102. For the purpose of authentication, a manufacturing detail may include at least one of production site, production date, production station, lot number, serial number, expiration date, any combination thereof, or any other identification key. According to some embodiments, once no manufacturing detail of the tubing is authenticated/identified, $CO_2$ sensing module 104 may be configured to terminate or suggest termination of usability of the tubing system. Alternatively, devoid authentication, the $CO_2$ sensing module 104 may fail to initiate. Additionally or alternatively, the $CO_2$ sensing module 104 may back-communicate data to the communication component 102, causing its abolishment/terminating its usability and/or change of its status when authentication is not validated, thus preventing potentially hazardous non-compatible use of the tubing system. According to some embodiments, the $CO_2$ sensing module 104 is further configured to transfer data based on the consumable authentication 116 to host the monitor 106 and/or the remote computing unit 108. According to some embodiments, the $CO_2$ sensing module 104 is configured to trigger a display of a user notification message 114 on the host monitor 106 notifying a user on authentication results and, optionally in case of an authentication problem, in conjunction with a message on termination of usage or a suggested termination of use. According to some embodiments, a user is allowed to implement, adjust, or overrule the suggested termination of use.

According to some embodiments, the $CO_2$ sensing module 104 is configured for consumable management 120 based on an information of a property of a tubing system 122 connected thereto received from the communication component 102 and to maintain, adjust, or suggest adjustment of an operation mode thereof to comply with the property of the tubing system. Non-limiting examples of properties include a length of a sampling tube, a diameter of the tubing system, a target group of the tubing system, an intended duration of use of the tubing system, or any combination thereof.

According to some embodiments, the $CO_2$ sensing module 104 is configured for consumable management 120 based on a usage data 124 of a tubing system connected thereto received from the communication component 102. Non-limiting examples of usage data include number of occlusions of the tubing system connected thereto, duration of use, number of uses/connections of the tubing system to a $CO_2$ sensing module, or any combination thereof. Once an upper limit of use has been reached and/or approached, the $CO_2$ sensing module 104 may trigger a display of a user notification message 114 on the host monitor 106 notifying the user of the tubing system having reached saturation, optionally in conjunction with a recommendation to discard the tubing system. According to some embodiments, the $CO_2$ sensing module 104 may back-communicate data to the communication component 102 causing its abolishment/terminating its usability and/or a change in its status, once an upper limit of use has been reached, thus preventing potentially hazardous continued use of the tubing system. Additionally or alternatively, the $CO_2$ sensing module 104 is configured for determining/monitoring a usage data of a tubing system connected thereto (option not shown). According to some embodiments, the $CO_2$ sensing module 104 may be further configured to transfer usage data 124 to the remote computational unit 108 and/or the host monitor 106 for storage and/or further analysis.

According to some embodiments, the remote computational unit 108 is configured for quality control 126 based on integration of a usage data 124 with a manufacturing detail 118, thereby enabling identification of manufacturing problems causing defects in the tubing system and/or enable identification of a defected tubing system prior to their use and/or distribution. According to some embodiments, the remote computational unit 108 is configured to back-communicate user instructions to the $CO_2$ sensing module 104 based on the quality control analysis.

As used herein, the terms "consumable" and "tubing system" are interchangeable.

Figure 2:
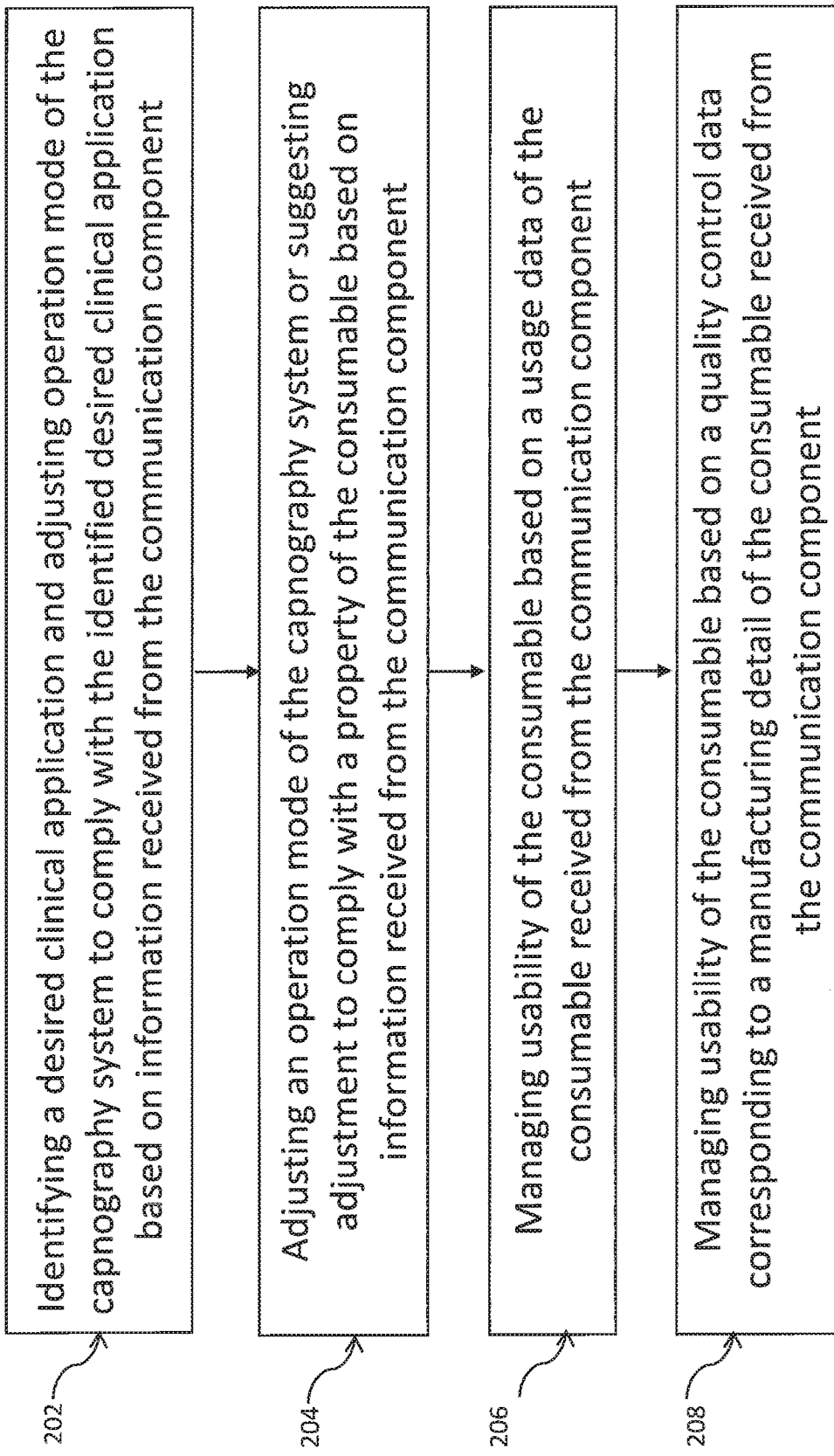
FIG. 2 is a flowchart of the steps of a method for capnography, according to some embodiments.

Reference is now made to FIG. 2, which is a flowchart of the steps of a method 200 for capnography, according to some embodiments. The method 200 may be carried out by the capnography system 100 of FIG. 1.

A desired clinical application is identified and operation mode of the capnography system is adjusted to comply with the identified desired clinical application based on information received from a communication component connected thereto (step 202). Optionally, the received information is an indication of a type of the consumable connected to the capnography system. An operation mode of the capnography system is adjusted or adjustment is suggested to comply with a property of the consumable based on information received from the communication component (step 204). Non-limiting examples of properties include a length of a sampling tube, a diameter of the tubing system, a target group of the tubing system, an intended duration of use of the tubing system, or any combination thereof. Usability of the consumable is managed based on a usage data of the consumable received from the communication component (step 206). Non-limiting examples of usage data include a number of occlusions of the tubing system connected thereto, a duration of use, a number of uses/connections of the tubing system to a $CO_2$ sensing module, or any combination thereof. Optionally, when an upper limit of use has been reached and/or approached, usability of the consumable is terminated or a termination is suggested. Usability of the consumable is managed based on a quality control data corresponding to a manufacturing detail of the consumable received from the communication component (step 208). Optionally, the usability of the consumable is maintained or terminated, or an operational mode may be adjusted to comply with operation of the consumable. Each of the options may be automatically performed or alternatively suggested to a user. Optionally, the quality control data is based on analysis of usage data of consumables with the same manufacturing detail. Optionally, the quality control data is analyzed by a remote computing system and communicated to the communication component.

Each of the steps may result in termination of use or in suggestion of termination of use. Each of steps 202, 204, 206, and 208 may be performed in an interchangeable order in parallel or in sequence. Furthermore, one or more of the steps 202, 204, 206, and 208 may be omitted from and/or additional steps may be added to the method 200.

For example, optionally, the method 200 further comprises a preliminary step of authenticating a consumable connected to a capnography system based on a manufacturing detail of the consumable. For the purpose of authentication, a manufacturing detail may include at least one of production site, production date, production station, lot number, serial number, expiration date, any combination thereof, or any other identification key. Optionally, when the manufacturing detail is not validated, the usability of the consumable may be terminated or termination of usability is suggested.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprises" or "comprising," when used in this application, specify the presence of stated features, integers, steps, operations, elements, or components, but do not preclude or rule out the presence or addition of one or more other features, integers, steps, operations, elements, components, or groups thereof.

Unless specifically stated otherwise, as apparent from the following discussions, it is appreciated that throughout the specification discussions utilizing terms such as "processing," "computing," "calculating," "determining," "estimating," or the like, refer to the action and/or processes of a computer or computing system, or similar electronic computing device, that manipulate and/or transform data represented as physical, such as electronic quantities within the computing system's registers and/or memories, into other data similarly represented as physical quantities within the computing system's memories, registers, or other such information storage, transmission, or display devices.

Embodiments of the present disclosure may include apparatuses for performing the operations herein. This apparatus may be specially constructed for the desired purposes, or it may comprise a general purpose computer selectively activated or reconfigured by a computer program stored in the computer. Such a computer program may be stored in a computer readable storage medium, such as, but not limited to, any type of disk including floppy disks, optical disks, compact discs with read-only memory (CD-ROMs), magnetic-optical disks, read-only memories (ROMs), random access memories (RAMs), electrically programmable read-only memories (EPROMs), EEPROMs, magnetic or optical cards, or any other type of media suitable for storing electronic instructions, and capable of being coupled to a computer system bus. For example, the current embodiments may be implemented by one or more computer processors that implement one or more machine-readable instructions stored on a tangible, non-transitory, machine-readable medium and/or by specialized circuitry designed to implement the discussed features. The processing unit may include one or more processors.

The processes and displays presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description herein. In addition, embodiments of the present disclosure are not described with reference to any particular programming language. It will be appreciated that a variety of programming languages may be used to implement the teachings of the embodiments as described herein.

The embodiments may be described in the general context of computer-executable instructions, such as program modules, being executed by a computer. Generally, program modules include routines, programs, objects, components, data structures, and so forth, which perform particular tasks or implement particular abstract data types. The embodiments may also be practiced in distributed computing environments where tasks are performed by remote processing devices that are linked through a communications network. In a distributed computing environment, program modules may be located in both local and remote computer storage media including memory storage devices.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

EXAMPLES

Reference is now made to the following examples which, together with the above descriptions, illustrate the embodiments in a non-limiting fashion.

Example 1

Figure 3:
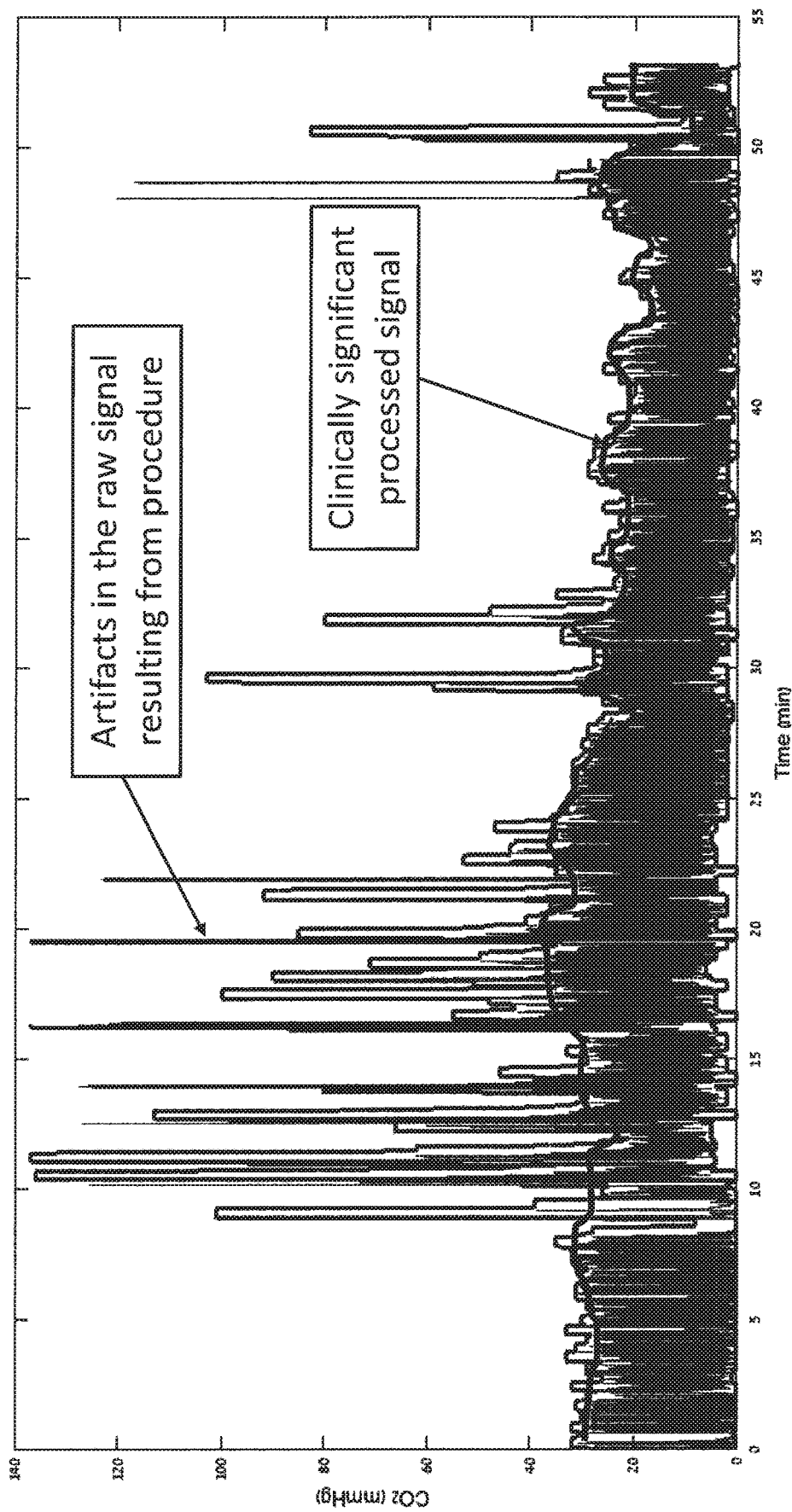
FIG. 3 is a graph showing experimental $CO_2$ readings measured during a $CO_2$ insufflation procedure.

Trials were performed in order to assess the efficiency and/or efficacy of utilizing a communication component for indicating use of the capnography system during a $CO_2$ insufflation procedure, thereby customizing operation of the capnography system to reduce $EtCO_2$ nuisance alarm during insufflation. To this end, the $CO_2$ sensing module was configured to include an algorithm capable of identifying and filtering out artifacts in the $CO_2$ concentration resulting from insufflation with $CO_2$ (rather than respiratory complications), the algorithm being dedicated for use in upper gastro-intestinal procedures utilizing bite block containing tubing. As demonstrated in FIG. 3, the modified $CO_2$ sensing module was capable of identifying the spikes as artifacts, thus confirming it as suitable for use in an operation mode customized for upper gastro-intestinal procedures, thereby reducing triggering of nuisance alarms.

It is noted that initial identification of the tubing system may be critical and/or useful prior to applying the algorithms. For example, filtering out artifacts during data processing, without prior identification of the tubing system, may not provide a desirable level of accuracy.

Example 2

Trials were performed in order to assess the efficiency and/or efficacy of utilizing the communication component for indicating use of the capnography system during emergency settings (EMS) in order to reduce time for verification of correct intubation. Customizing the operation mode of capnography systems to include there herein disclosed communication component resulted in a reduction in the average time for verification of correct intubation by approximately 25 percent and 12 percent, regardless of tubing length. The pump in capnography modules, as in other electromechanical devices, is often designed to work at/around an optimal point, below its full capacity. This may be the pump's best efficiency point or set according to a desire to reduce the pump size or minimize acoustic noise generated by the pump. Since the pump is not operating at full capacity under normal conditions, it is possible to increase the pump's output, thus increasing the flow of the sampled air, thereby reducing the response time. Increasing the pump's output to its full limit (e.g., upper limit) is permissible over short intervals of time; however, continued operation of the pump at the full limit of the pump's output may adversely affect system operation (e.g., reliability, wear). Additionally, increasing the flow of the sampled air may not be suitable for some patient populations, such as neonates. Accordingly, the ability of the system to identify the tubing system, and to activate the "maximum pump output" feature only when a tubing system intended for use with certain types of patients (e.g., adult patients) is identified, may provide various advantages.

The invention claimed is:

1. A method of operating a capnography system, comprising:
   receiving, at one or more processors, first data indicative of a carbon dioxide ($CO_2$) concentration in exhaled breath of a subject from a $CO_2$ sensor of a $CO_2$ sensing system and second data indicative of information associated with a tubing system in response to the tubing system being coupled to the $CO_2$ sensing system, wherein the second data is received from a communication component associated with the tubing system; and
   changing, by the one or more processors, an operation mode of the $CO_2$ sensing system during operation of the $CO_2$ sensing system based on the second data indicative of the information associated with the tubing system.

2. The method of claim 1, wherein the second data comprises an indication of a property of the tubing system, the method further comprising:
   changing, by the one or more processors, the operation mode of the $CO_2$ sensing system based on the indication,
   wherein the property of the tubing system comprises a length of the tubing system, a diameter of the tubing system, a target group of the tubing system, an intended duration of the tubing system, or any combination thereof.

3. The method of claim 1, wherein the second data comprises an indication of a manufacturing detail of the tubing system, the method further comprising:
   changing, by the one or more processors, the operation mode of the $CO_2$ sensing system based on the indication,
   wherein the manufacturing detail of the tubing system comprises a production site, a production date, a production station, a lot number, a serial number, an expiration date, or any combination thereof.

4. The method of claim 1, further comprising:
   determining, by the one or more processors, a change of the operation mode based on the second data indicative of the information associated with tubing system;
   sending, by the one or more processors, the change in the operation mode of the $CO_2$ sensing system to a user interface associated with the $CO_2$ sensing system; and
   causing display, by the one or more processors, of the change of the operation mode on the user interface associated with the $CO_2$ sensing system.

5. The method of claim 1, wherein the tubing system comprises an intubation tube, and wherein changing the operation mode of the $CO_2$ sensing system comprises causing, by the one or more processors, an increase in a speed of a pump of the $CO_2$ sensing system upon intubation of the subject and until a first $CO_2$ signal is obtained by the $CO_2$ sensor.

6. The method of claim 1, wherein the tubing system comprises a bite block, and wherein changing the operation mode of the $CO_2$ sensing system comprises, by the one or more processors, at least one of identifying $CO_2$ concentration peaks resulting from insufflation of the subject, and initiating use of an algorithm configured to reduce nuisance alarms during insufflation.

7. The method of claim 1, wherein the tubing system comprises an oral nasal cannula, and wherein changing the operation mode of the $CO_2$ sensing system comprises, by the one or more processors, at least one of identifying a high respiration rate resulting from pain, initiating use of an algorithm configured to reduce nuisance alarms during pain management.

8. The method of claim 1, further comprising, determining, by the one or more processors, one or more breath related parameters based on the first data indicative of the $CO_2$ concentration, wherein changing the operation mode of the $CO_2$ sensing system comprises, by the one or more processors, at least one of identifying aberrations in $CO_2$ measurements resulting from dilution of the exhaled breath with oxygen, initiating use of an algorithm configured to at least one of correct, normalize, or adjust the one or more breath related parameters based on the dilution.

9. The method of claim 1, further comprising:
   receiving, at the one or more processors, usage data based on the second data indicative of the information associated with the tubing system, wherein the usage data comprises a number of occlusion of the tubing system, a duration of use, a number of uses/connections of the tubing system to the $CO_2$ sensing system, a number of uses/connections of the tubing system to an additional $CO_2$ sensing system, or any combination thereof;
   generating, by the one or more processors, a signal terminating usability of the tubing system, in response to determining, based on the usage data, that the tubing system has run obsolete; and
   causing, by the one or more processors, transmission of the signal to the communication component associated with the tubing system.

10. The method of claim 9, wherein the signal terminating the usability of the tubing system is configured to adjust a status associated with the tubing system, the method further comprising:
    receiving, at the one or more processors, an indication of the adjusted status associated with the tubing system;
    inactivate, by the one or more processors, the $CO_2$ sensing system; and
    cause, by the one or more processors, display of a notification indicating the adjusted status associated with the tubing system.

11. The method of claim 1, wherein changing the operation mode of the $CO_2$ sensing system comprises changing an operation of a pump associated with the $CO_2$ sensing system based on the second data indicative of the information associated with the tubing system.

12. The method of claim 1, wherein the second data comprises an indication of operational data associated with the tubing system and a manufacturing detail of the tubing system, the method further comprising transferring, by the one or more processors, the second data to a remote computational unit communicatively coupled to the capnography system.

13. The method of claim 12, wherein the remote computational unit is configured to integrate the operational data with the manufacturing detail, thereby enabling identification of a defective tubing system prior to use or distribution of the defective tubing system.

14. The method of claim 1, wherein the communication component comprise a 1-wire electrically erasable programmable read-only memory (EEPROM).

\* \* \* \* \*